United States Patent [19]

Nash et al.

[11] 4,315,742

[45] Feb. 16, 1982

[54] VIBRATORY DEVICE HAVING TOOL ASSEMBLY WITH FLUID TRANSPORT MEANS

[75] Inventors: John E. Nash, Downingtown; Arthur A. Knopp, Chalfont, both of Pa.

[73] Assignee: Syntex (U.S.A.) Inc., Palo Alto, Calif.

[21] Appl. No.: 91,012

[22] Filed: Nov. 5, 1979

[51] Int. Cl.³ .......................... A61C 1/10; A61C 1/12; A61C 1/07; A61C 17/02
[52] U.S. Cl. ....................................................... 433/86
[58] Field of Search ................................. 433/86, 119

[56] References Cited

U.S. PATENT DOCUMENTS 3,375,583 4/1968 Blank et al. ............................ 433/86
3,518,766 7/1970 Burt ..................................... 433/119

*Primary Examiner*—Robert Peshock
*Attorney, Agent, or Firm*—John A. Dhuey; Joseph I. Hirsch

[57] ABSTRACT

An air-driven dental scaler is disclosed having water transport means associated with the tool assembly for delivering water to a scaling type work tool. The water transport means comprises a tube disposed within a hollow connector body and extending between a water plenum at one end of the connector body to the other end of the connector body, whereat the scaling type work tool is attached. The water transport tube has an internal diameter of greater than 0.010 inch and a surface roughness smoother than 25 micro-inches to minimize clogging of the tube by mineral deposits or sediment. The independent fluid path permits the use of hard, martensitic stainless steels for the work tool and softer, corrosion-resisting austenitic stainless steels for the water transport tube. The water transport means delivers a controlled quantity of water to the work tool and the water is atomized by the vibratory movement of the tool.

22 Claims, 8 Drawing Figures

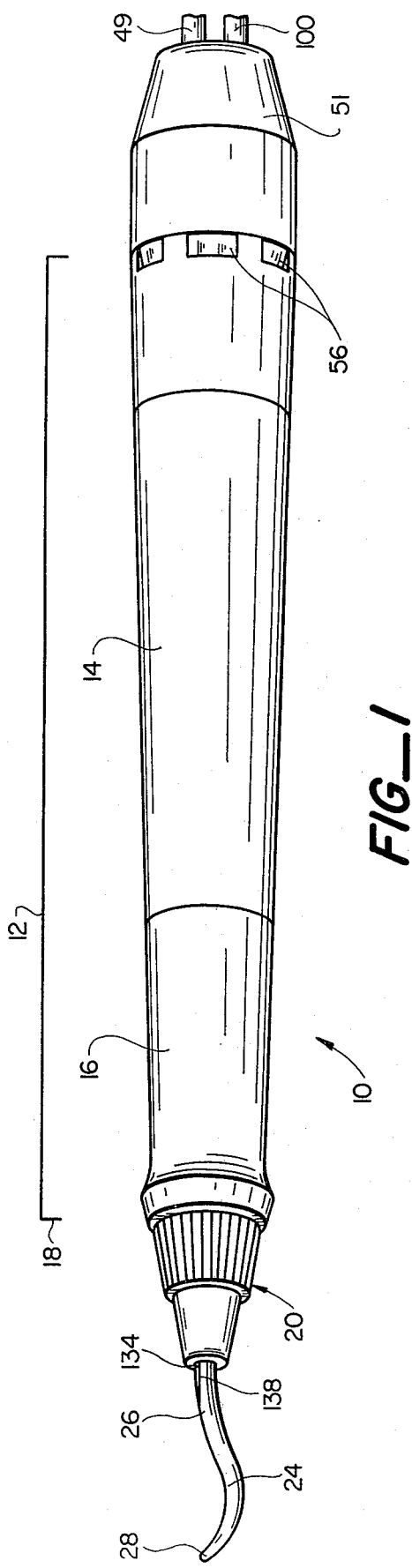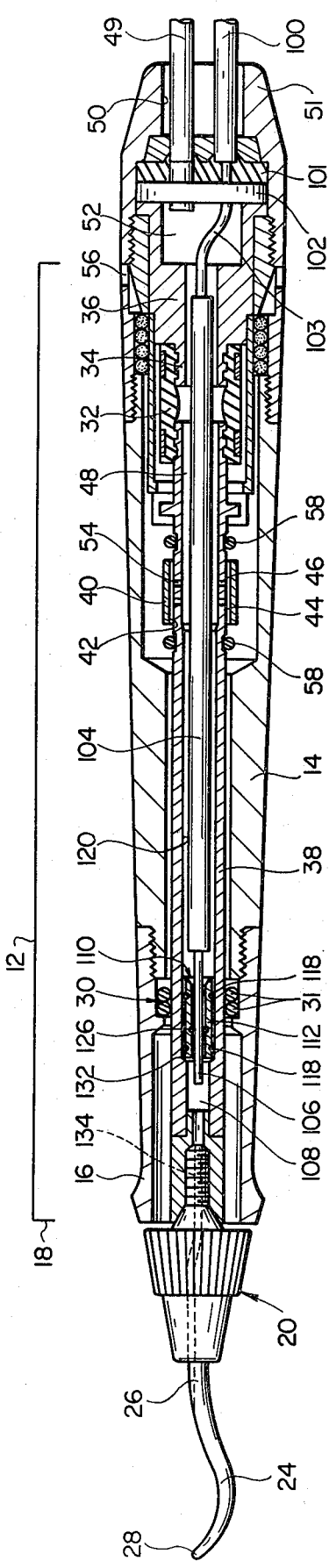

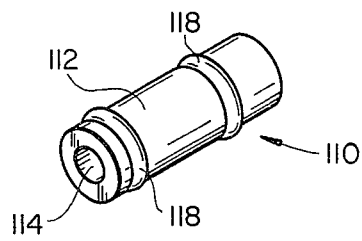
FIG_3
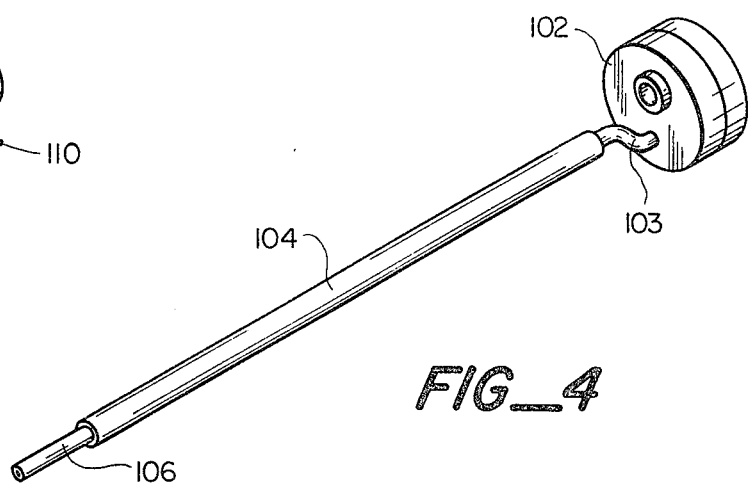
FIG_4
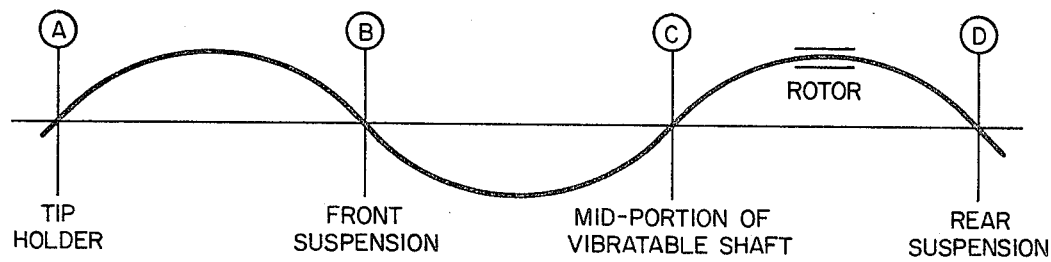
FIG_5
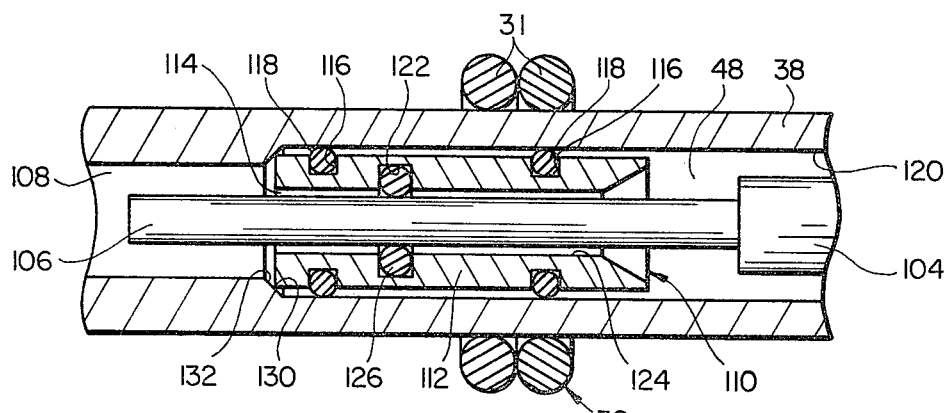
FIG_6
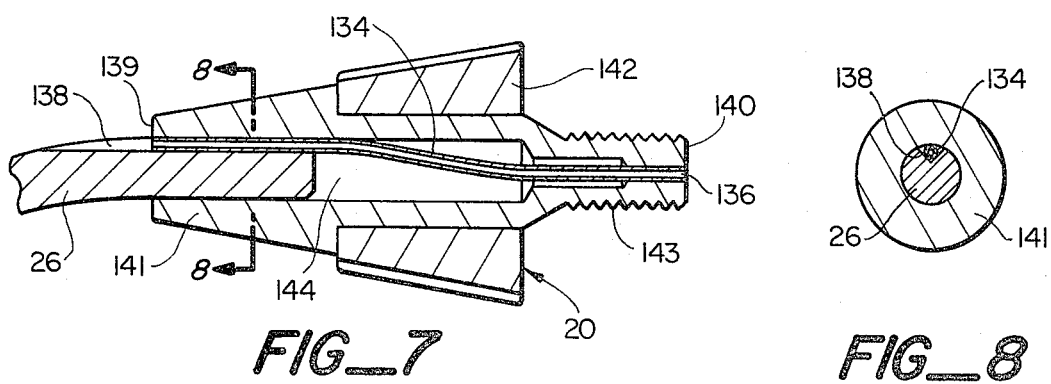
FIG_7
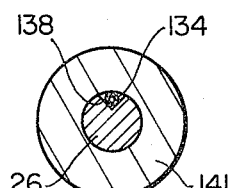
FIG_8

VIBRATORY DEVICE HAVING TOOL ASSEMBLY WITH FLUID TRANSPORT MEANS

BACKGROUND OF THE INVENTION

1. Field

Power driven dental scalers are well known. Of particular interest herein is a dental scaler having a vibratable scaling work tool for removing calculus, stain or plaque from teeth, which dental scaler utilizes a stream of water to aid in scaling efficiency and in removal of accumulated debris.

2. State of the Art

Of the power driven dental scalers currently available, most common are scalers utilizing a flow of compressed air or a solid-state ultrasonic transducer to cause a scraping type work tool to vibrate.

Typical of the earlier air-driven dental scalers are those of U.S. Pat. No. 3,082,529 and U.S. Pat. No. 3,444,622 to Mills et al, which scalers utilize an air-driven ball contained in a chamber. Movement of the ball against the walls of the chamber imparts vibration to the chamber, which vibrations are then transmitted to the scraping tool. A more recent type of air-driven scaler, described in U.S. Pat. No. 3,526,962 to Fuerst, utilizes a rotatable mandrel which has an irregularly-shaped tip engaged with a reciprocable block in which the mandrel tip is received.

It is characteristically a problem of these air driven scalers that much of the vibrational energy generated by the vibrator motor is transferred to the handle portion of the dental scaler rather than to the scraper work tool. Moreover, the modes of vibration of these scalers may change as moving parts of the vibration generating mechanism wear with time.

In U.S. Pat. No. 3,703,037 to Robinson, there is described a dental scaler which utilizes a solid state ultrasonic transducer to provide constant modes of vibration for coupling with particular types of work tools. One disadvantage of the ultrasonic scaler, however, is the cost of the transducer and its fairly sophisticated ultrasonic generator.

A different air-driven dental scaler is disclosed in U.S. Pat. No. Re. 29,687 to Sertich. This dental scaler has very few moving parts as compared to the aforementioned mechanically complicated air-driven scalers and provides efficient transfer of vibrational energy to a scraping-type work tool with relatively little vibration being transferred to the handle portion of the instrument. Moreover, this type of scaler provides uniform modes of constant vibration which may be matched with the vibratory modes of various types of work tools without the need for complicated electronic components.

It has been found that a flow of water over a tooth surface can provide increased scaling efficiency and patient comfort by lubricating and cooling the tooth surface and by flushing scaled debris and blood from the surface and area being cleaned. A work tool having a fluid path therethrough is described in U.S. Pat. No. 3,368,280 to Friedman et al. The fluid path consists of a narrow bore in the shank of the work tool itself or a bore in the wall of the work tool connector designed to direct the fluid flow over the dog leg of the work tool to impinge on the tip. A disadvantage of the Friedman device is that it is extremely difficult to accurately machine a narrow bore in the shank of the work tool, particularly when it is made of very hard materials, or to machine within the wall of the tool connector itself. Additionally, the bore opens into a plenum in the connector itself, resulting in a discontinuous inner surface which can cause an increase in the collection of debris and make cleaning difficult.

A solid state type dental scaler utilizing a flow of water to improve cleaning efficiency is described in U.S. Pat. No. 4,038,571 to Hellenkamp. One disadvantage of the Hellenkamp device, in addition to that of relatively high cost, is the shock hazard associated with the use of both electrical power and water in a hand-held instrument.

U.S. Pat. No. 3,375,583 (Blank et al) is directed to an ultrasonic dental tool having a work tool with a threaded end for engagement with a work holder member and an axial bore, which is counter-bored to receive a work tool element and a tube for transfer of water therethrough to impinge in a spray form on the extreme terminal end of the work tool. The tube extends out of the work tool, bridging substantially the entire length of the work tool element, to direct water onto the extreme terminal end of the work tool element. One disadvantage of the work tool described by Blank et al is that the water tube does not extend continuously between the ends of the work tool. Consequently, sediment and mineral deposits can collect in the area of the junction of the bore and counter-bore, and proper cleaning of the work tool in that area is difficult. Furthermore, the water tube extents into the work area of the work tool element where it can interfere with the proper operation of the work tool element on the teeth of a patient.

U.S. Pat. No. 3,075,288 (Balamuth et al) describes a dental instrument having an internal feed of water to the work area. A work tool holder is provided with a longitudinal passage intersecting a radial passage at its inner end which is normally closed by a valve. Actuation of the valve permits water to flow through the radial passage, into the longitudinal passage, through a slot in the work tool and over the work tool surface. That construction is not entirely satisfactory since the discontinuous surfaces are difficult to clean and tend to collect sediment and deposits.

It would be desirable to have a non-electrical, air-driven dental scaler having means for delivering water to the scaler tip which does not interfere with the operation of the scaler tip in the work area. Of particular advantage would be a relatively low-cost air-driven dental scaler having the scaling efficiency advantages of the "Sertich-type" scaler together with the advantage of water flow at the scaler tip to enhance the cleaning action.

A particular problem which occurs frequently in the use of dental instruments utilizing water transport tubes with small bores (such as 0.020 inch or less) is clogging of the tube with sediment or minerals carried in the stream of water. Hence, it is of benefit for a scaler to have a water supply tube that is easily accessible and can be cleaned quickly in the event it becomes clogged.

There is need, therefore, for an air-driven dental scaler having fluid transport means incorporated in the work tip assembly for delivering water to a scaling tip which is less prone to clogging and which can be easily and completely cleaned in the event clogging occurs.

SUMMARY OF THE INVENTION

A work tool assembly for a vibratory device is provided which comprises a hollow body having a first end and a second end, the first end of the body being adapted for attachment to a vibratory device and having a first orifice therein, the second end of said body having a second orifice therein; a substantially cylindrical tube having a first end and a second end, the tube extending continuously from the first end of the body to the second end of the body, the first end of the tube being located within the first orifice; and a work tool having a first end and a second end, the first end of the tool being adapted for insertion into the second end of the body within the second orifice, the second end of the tool being adapted for performing an operative function on a tooth surface, the tool having a groove on the outer surface thereof extending from the first end of the tool to a position intermediate the first and second ends of the tool and outwardly of the second end of the body, a portion of the tube lying within the groove between the tool and the body, thereby establishing a continuous fluid path from the first end of the body to the second end of the body to convey fluid to the groove and the outer surface of the tool.

In another aspect of the invention, an air-driven vibratory-type dental scaler is provided which comprises elongated casing means having a proximal end and a distal end; resilient support means within the casing means; a substantially rigid hollow shaft supported within the elongated casing means by the resilient support means; work tool assembly means attached to the distal end of the hollow shaft, the work tool assembly means comprising a hollow body having a first end and a second end, the first end being adapted for attachment to the hollow shaft and having a first orifice therein, the second end of the body having a second orifice therein, a tube having a first end and a second end, the tube extending continuously from the first end of the body to the second end of the body, the first end of the tube being located within the first orifice, and a work tool having a first end and a second end, the first end being adapted for insertion into the second end of the body within the second orifice, the second end of the tool being adapted for performing an operative function on a tooth surface, the tool having a groove on the outer surface thereof extending from the second end of the tool to a position intermediate the first and second ends of the tool and outwardly of the second end of the body, a portion of the tube lying within the groove between the tool and the body; means for imparting vibration to the resiliently supported hollow shaft when the dental scaler is energized to provide vibratory movement to the work tool; second water transport means associated with the casing means comprising a tube disposed substantially coaxially within the hollow shaft, the tube having a proximal end and a distal end; and a water seal assembly for supporting the distal end of the water transport tube within the hollow shaft. The dental scaler can have a vibrational node near the distal end of the hollow shaft, the water seal assembly disposed forwardly of the vibrational node at a distance up to about one-quarter of a vibrational wavelength, preferably about one-sixteenth to about one-quarter of a vibrational wavelength.

The dental scaler may include elongated casing means having a proximal end and a distal end, resilient support means within the casing means, a substantially rigid hollow shaft supported within the elongated casing means by the resilient support means, work tool connecting means attached to the distal end of the hollow shaft, the work tool connecting means capable of operatively connecting a work tool to the distal end of the hollow shaft, first water transport means associated with the work tool connecting means, the first water transport means comprising a tube extending continuously from the proximal end to the distal end of the connector means and being retained between the connector means and the work tool at the distal end of the connector means, means for imparting vibration to the resiliently supported hollow shaft when the dental scaler is energized to provide vibratory movement to a work tool connected to the work tool connecting means, second water transport means associated with the casing means comprising a tube disposed substantially coaxially within the hollow shaft, support means for detachably supporting the water transport tube within the hollow shaft including sealing means disposed about the distal end of the tube for forming a water-tight seal between the hollow shaft and the water transport tube and flexible connecting means within the elongated casing means for detachably connecting the proximal end of the water transport tube to an external source of water.

The hollow shaft can have shoulder means disposed upon an inner wall portion thereof, the shoulder means being disposed forwardly of the vibrational node, and the sealing means including a cylindrically-shaped body in contact with the shoulder means and having a plurality of annular grooves each of which contains an O-ring such that water-tight seals are established with the adjacent surfaces of the hollow shaft and the water transport tube.

Dental scalers as described herein have an easily accessible and replaceable water transport tube within the work tool connector assembly. It is, therefore, quite compact and does not interfere with the vibratory pattern characteristic of this type of dental scaler.

DESCRIPTION OF PRESENTLY PREFERRED EMBODIMENTS

FIG. 1 is a perspective view of a dental scaling instrument of this invention;

FIG. 2 is a longitudinal side elevational view, partly in section, of the dental scaler of FIG. 1;

FIG. 3 is a perspective view of a water seal assembly suitable for sealing the water transport tube within the dental scalers of FIGS. 1 and 2;

FIG. 4 is a perspective view of the water transport tube shown in FIGS. 1 and 2;

FIG. 5 is a schematic representation of a typical standing wave generated by a Sertich-type dental scaler illustrating the position of vibratory nodes within the scaler body;

FIG. 6 is an enlarged fragmentary view of the water seal assembly which provides a water tight seal between the vibratory shaft and the water transport tube;

FIG. 7 is a side sectional view of the nose piece and work tool associated with the scaler of FIG. 1 showing the fluid transport means associated with the work tool connector and the groove on the work tool for directing water from the water transport tube to the end of the scaling tip; and FIG. 8 is a cross-sectional view along line 8—8 of FIG. 7.

Illustrated in FIG. 1 is a dental scaling instrument 10 comprising a handle 12 which includes a barrel 14 and a neck 16. Attached to the distal end 18 of scaler 10 is the work tool assembly of the present invention, which is illustrated most clearly in FIGS. 7 and 8. That assembly generally comprises a connector designated 20 formed from an inner hollow body 141 and a knurled, outer knob 142. Knob 142 typically is press fit onto body 141 and provides a readily available area for grasping of connector 20 by an operator for attachment to distal end 18 of scaler 10. Body 141 has a threaded portion 143 for attachment to shaft 38 of scaler 10. End 140 includes a substantially cylindrical orifice 136 into which a first end of a tube 134 extends. A second end 139 of body 141 includes a substantially cylindrical orifice 144 into which the second end of tube 134 and shank 26 of tool 24 extend. The second end of tube 134 and a portion of tube 134 adjacent that end are secured within opening 144 of body 141 and positioned in a groove 138 in work tool 136. Groove 138 extends from the first or proximal end of work tool 26 toward the second or distal end of tool 26, to a position intermediate said first and second ends of tool 26 and outwardly from the end 139 of body 141. In that manner, water can be transported from end 140 of body 141 to end 139 of body 141 in a continuous conduit.

As shown most clearly in FIG. 8, groove 138 typically is V-shaped and tube 134 is substantially cylindrical. The outside diameter of work tool 26 is of substantially the same dimension as the inside diameter of body 141 at end 139. The outer diameter of tube 134 is chosen to fit within the space created by groove 138 and the inner wall of body 141.

An important feature of the present invention is that tube 134 establishes a smooth continuous fluid flow path from end 140 to end 139 of body 141. Establishment of a continuous flow path minimizes areas in which sediment or debris from the flowing fluid can collect. Additionally, the smooth inner surface of tube 134 minimizes deposition of mineral deposits from the water. It is presently preferred that the inner surface of tube 134 have a surface smoothness of 25 micro-inches or better. Furthermore, the internal diameter of tube 134 should be between about 0.010–0.018 inch in order to minimize problems from clogging with sediment and minimize excessive water transport to the scaling tip which can cause discomfort to the patient.

The structure of the work tool assembly of the present invention is adapted to utilize different materials in the fluid transport system and the work tool itself. In contrast to prior art devices having a bore or cavity within the work tool for transport of fluid, the present invention utilizes a flow path which is independent of the work tool itself. Accordingly, it is possible to use different materials for the work tool and the fluid transport means to accomplish their individual purposes in an efficacious manner. In most applications, it is desirable to have work tool 26 formed of a hard material so that it wears little during abrasion or impacting on materials on the tool surface in which it comes in contact. Typical, tool 26 is formed from the martensitic stainless steels which can be hardened by heat treatment to increase their tensile strength above that in the untreated state. A problem associated with such steels however, is that they tend to exhibit inferior corrosion resistance. The constant flow of water in a bore or fluid pathway developed in a tool of the prior art which is formed from martensitic alloys, typically will undergo surface corrosion to form debris which tends to block the fluid transport bore. That deficiency in the prior art is avoided in the present invention, since it is possible to utilize a more non-corrosive stainless steel such as an austenitic stainless steel in the fluid tube 134 contemplated herein. Thus, the advantages of using a martensitic steel for work tool 26 and a more non-corrosive austenitic stainless steel for tube 134 can be advantageously employed. Illustrative of the austenitic stainless steels are the type 300 series including type 302, 303, 304 and 316 stainless steels. Illustrative of the martensitic stainless steels are those of type 400 including type 416 and 440C stainless steels. For dental applications a work tool formed of type 416 stainless steel has been eminently satisfactory.

In order to facilitate manufacture of the work tool assembly of the present invention, orifice 136 is sized to provide a clearance fit with the outside surface of tube 134. During assembly tube 134 and work tool 26 are pressed into body 141 in a direction toward the proximal end of scaler 10. Because orifice 136 establishes a clearance fit with tube 134 there is no difficulty in tube 134 passing through the orifice and being aligned therewith when the tip and tube assembly are pressed into body 141. When work tool 26 and tube 134 have been completely inserted into body 141, any excess tubing extending outwardly from end 140 of body 141 can be conveniently removed to make the first end of tube 134 flush with end 140 of body 141. The second or distal end of tube 134 can be flush with end 139 of body 141 or it can extend a small distance outwardly therefrom into groove 138 as long as the water flows into groove 138 and flows over and contacts the surface of work tool 26 as it proceeds to tip 28.

As will be described more fully hereinafter, during operation of the scaler when water seal assembly 110 is in contact with shoulder 132, plenum 108 receives water from tube 103 for delivery to the work tool assembly. Water flows from plenum 108 through tube 134 to the distal end of body 141 where the water then flows into groove 138 of work tool 26. The water flows over the surface of work tool 26 toward the terminal end 28 and is atomized by the vibratory motion of tip 28. The water mist so created provides lubrication, a cooling effect on the tooth surface upon which tool 26 is being applied and soothing effect to the patient.

As shown in detail in the cross-sectional view of FIG. 2, handle 12 provides an elongated casing within which is mounted resilient support means comprising a first or front resilient support 30 including a pair of O-rings 31. A second or rear resilient support is provided by a cylindrical tube 32 of resilient material which is sleevably engaged about a boss portion 34 secured to a rigid rear support 36. Disposed substantially coaxially with respect to elongated handle 12 is a vibratable, substantially rigid, hollow shaft 38. Connector 20 is attached to the distal end of hollow shaft 38.

Disposed about a mid-portion of shaft 38 is a sleeve-like rotor 40. As shown in FIG. 2, during operation of the scaler, rotor 40 rotates about shaft 38, and establishes a gap 42 between rotor 40 and an adjacent portion of side wall 44 of shaft 38. In an actual assembly with rotor 40 at rest, rotor 40 will be supported upon shaft 38 so that a portion of rotor 40 will rest upon side wall portions of shaft 38. Located in side wall portions of shaft 38 are a plurality of outlet ports 46 which connect passageway 48 of shaft 38 to gap 42.

As indicated by the arrows in FIG. 2, a fluid medium, such as compressed air, is supplied from a source (not shown) through a supply tube 49 which passes through an axially disposed opening 50 in end cap 51. The flow of compressed air passes into plenum 52 and through passageway 48 to fluid media outlet ports 46. The flow of compressed air which exhausts through outlet ports 46 strikes the inner wall of rotor 40 and urges rotor 40 to rotate about shaft 38. Each of outlet ports 46 has an axis which is offset or spaced at a distance from the longitudinal axis of shaft 38, such that each port axis does not intersect the axis of shaft 38. Thus each of ports 46 directs a jet of air at a glancing angle with respect to the inner wall of rotor 40 so as to impart rotary movement to rotor 40.

After imparting rotary movement to rotor 40, the air exhausts through the gap 42 between rotor 40 and shaft 38 and is then exhausted from the interior of barrel 14 through exhaust ports 56 disposed circumferentially about a rearward portion of barrel 14. Stop means comprising an annular-shaped guide 58 affixed to shaft 38 prevents excessive travel of rotor 40 in an axial direction toward the forward or distal end of shaft 38 so that rotor 40 will at all time have at least a portion thereof disposed over outlet ports 46. A further description of the manner in which the spinning rotor 40 imparts vibration to shaft 34 may be found in the aforementioned U.S. Pat. No. 29,687, the disclosure of which is incorporated herein by reference.

The dental scaler further includes means for transporting water from an external source to work tool 24 and its curved end 28. A first water transport hose 100 located at the rearward or proximal end of scaler 10 is mounted in a detachable coupling 101. First water hose 100 is connected to an external source of water (not shown), the forward end of the hose being connected to one end of a rigid tube 103 which passes through a passageway in support body 102. Tube 103 is disposed substantially coaxially with respect to hollow shaft 38. Water transport tube 103 extends through hollow shaft 38 toward the distal end of scaler 10 and terminates distally from water seal assembly 110. Tube 103 is covered with an elastomeric tube covering 104 to eliminate vibration build-up within tube 103. The forward or distal end 106 of water tube 103 extends into plenum 108.

Water tube end 106 is supportably received within a water seal assembly 110 located at the forward or distal end of dental scaler 10. As shown in more detail in FIGS. 3 and 6, water seal assembly 110 comprises a cylindrical body 112 having a passageway 114 coaxially disposed with respect to the axis of body 112. Running circumferentially about the outer side wall of cylindrical body 112 are a pair of spaced annular grooves 116, one adjacent each end of cylindrical body 112. Disposed within each of grooves 116 is an O-ring 118 fabricated of a resilient material. O-rings 118 serve to position cylindrical body 112 within the forward end of hollow shaft 38 by frictional engagement of O-rings 118 with portions of inner wall 120 of hollow shaft 38. Within a mid-portion of cylindrical body 112 is a chamber formed by an annular groove 122 running circumferentially along a portion of inner wall 124 between grooves 116. Contained within groove 122 is an O-ring 126 which is in frictional engagement with the walls of groove 122 and with a portion of water tube end 106. O-ring 126 helps to properly position tube 103 centrally within hollow shaft 38.

Water seal assembly 110 provides a resilient support for water transport tube 103 within vibratable hollow shaft 38 by means of O-rings 118 and 126. Also, O-rings 118 and 126 provide a water-tight connection between plenum 108 and air passageway 48 within hollow shaft 38.

The water seal assembly 110 and water transport tube 103 are easily replaceable in the event of failure of one of the sealing O-rings or of clogging of the water tube. A good water-tight seal is ensured by the sealing contact of the O-rings forming part of water seal assembly 110 with the adjacent portions of vibratable hollow shaft 38 and water tube 103. Illustrated in FIG. 5 is a schematic representation of a standing wave pattern generated within the dental scaler by vibration of shaft 38 at a frequency typically at about 6000 Hz. The standing wave characteristically has four vibrational nodes occurring at points "A", "B", "C" and "D". Node "A" occurs within or adjacent a portion of nose piece 20, node "B" within front suspension 30, node "C" at a mid-portion of vibratable hollow shaft 38 and node "D" close to rear suspension 32. Placement of the water seal assembly 110 close to a vibrational node (e.g., node "B") minimizes the amount of vibrational energy transferred to water tube 103 from hollow shaft 38, which transfer of vibration would drain energy from the vibrating shaft while at the same time cause turbulence within the water tube and/or possible vibratory failure of the tube.

By positioning the center of gravity of water seal assembly 110 slightly forwardly of node "B", that is, toward the distal end of scaler 10, annular edge 130 of cylindrical body 112 is maintained in contact with a shoulder 132 in a wall portion of shaft 38. Provided water seal assembly 110 is so positioned with its center of gravity forward of node "B", the centrifugal conical whirl of shaft 38 during its vibratory movement imparts a force on cylindrical body 112 tending to move body 112 in a forward axial direction toward the distal end of scaler 10, which axial force ensures continuous contact between cylindrical body 112 and shoulder 132 without the need for supplemental retaining means. The magnitude of the axial force, $F_A$, acting on cylindrical body 112 may be calculated by the following equation $$F_A = mr\omega^2 \tan \alpha$$

wherein "m" is the mass of the water seal assembly, "r" is the radius of the orbit of revolution traced by the portion of the vibrating shaft for the particular axial position of the water seal assembly with respect to a node, "$\omega$" is the orbital speed of that portion of the vibratable shaft and "$\alpha$" is the angle established between the conically whirling vibratable shaft and the axis of the revolution of the shaft. This axial retaining force is especially needed to hold water seal assembly 110 in place when rotor 40 coasts to a standstill after the driving fluid is turned off, at which time there is no driving fluid pressure acting on assembly 110 to hold body 112 in its forwardmost distal position. The distance the water seal assembly should be positioned along the axis forward of node "B" can be related to the frequency of vibration, $\omega$. This distance forward of node "B" is up to about one-quarter of a vibrational wavelength, generally about one-sixteenth to about one-quarter of a vibrational wavelength, with the axial position of the center of gravity of the water seal assembly preferably being at a distance of just less than about one-quarter wavelength forward of the vibrational node.

The improvement of this invention can be utilized with a dental scaler or vibratory device of the type described in Sertich U.S. Pat. No. 29,687 or copending application Ser. No. 091,016, Nov. 5, 1979, entitled "Rotor Driven Vibratory Device Having Rotor Centralization Means and Vibrational Mode Selection Means Associated Therewith," filed concurrently herewith. If desired such a dental scaler or vibratory device can be further modified in accordance with the teachings of either or both of copending applications Ser. Nos. 12,631, filed Feb. 16, 1979, or 26,378, filed Apr. 2, 1979. Scaling tips suitable for use with such dental scalers or vibratory devices can be, for example, as shown in copending applications Ser. No. 091,013, Nov. 5, 1979, entitled "Dental Scaler Having Scaling Tip Particularly Suitable For Circular or Ellipsoidal Patterns of Vibration" and Ser. No. 091,018, Nov. 5, 1979, entitled "Dental Scaler Having Scaling Tip With Rounded Edge Work Surfaces Particularly Suitable For Circular or Ellipsoidal Patterns of Vibration," filed concurrently herewith. The above applications are incorporated herein by reference to the extent necessary to supplement or complete the disclosure hereof.

Although this invention has been described with reference to the incorporation of means of transporting water through the dental scaler of this invention, it is also contemplated that other fluids, such as medicaments (e.g., caries-removing liquids) or prophalytic or therapeutic agents (e.g., liquid fluoride compositions) compatible with dental practice can be used in conjunction therewith.

Although this invention has been described with reference to a dental scaler, it is also applicable to vibratory devices of like or similar configuration which are used for other purposes, such as medical, veterinary, and general industrial cleaning, polishing and deburring, etc. Such vibratory devices can have water, air, paraffin or other fluid materials transported therethrough in accordance with the teachings of this invention.

By centrally or axially positioning the water transport means of this invention within the vibratable hollow shaft and within the work tool assembly, the overall size and dimension of the scaler does not change; therefore, good weight balance and tactile control are retained, and the scaler stays sufficiently small to be inserted, without undue comfort, into the patient's mouth. In addition, by supporting the water transport means and the vibratable shaft in the manner as shown, energy losses through transfer of vibration from the shaft to the water tube are minimized, as is generation of noise which might be objectionable to both operator and patient alike. Through use of the detachable coupling 101, the water seal assembly 110, the water transport means in the work tool assembly, and the associated elements, as described herein, the water supply function is obtained in a manner which is readily repaired or replaced if the need arises.

While this invention has been described with reference to specific embodiments thereof, it should be understood by those skilled in this art that various changes may be made and equivalents may be substituted without departing from the true spirit and scope of the invention. In addition, various novel elements, as described herein, can be used individually or collectively, as desired. All such modifications are intended to be within the scope of the claims appended hereto.

What is claimed is:

1. A work tool assembly for a vibratory device comprising:
   a hollow body having a first end and a second end, said first end being adapted for detachable connection to a vibratory device and having a first orifice therein, said second end of said body having a second orifice therein;
   a tube having a first end and a second end, said tube extending continuously from said first end of said body to said second end of said body, said second end of said tube terminating substantially adjacent to the second end of said body, said first end of said tube being located within said first orifice and terminating flush with said first end of said body; and
   a work tool having a first end and a second end, said first end of said tool being adapted for insertion into said second end of said body within said second orifice, said tool having a groove on the outer surface thereof extending from said first end of said tool to a position intermediate said first and second ends of said tool and outwardly of said second end of said body, a portion of said tube lying within said groove between said tool and said body, thereby establishing a continuous fluid path from said first end of said body to said second end of said body to convey fluid into said groove and in contact with the outer surface of said tool whereby the fluid is transferred along the outer surface of said tool to said second end of said tool.

2. The work tool assembly of claim 1 wherein said tube has an internal diameter of between about 0.010 and 0.018 inches.

3. The work tool assembly of claim 1 wherein said tube has an internal diameter of about 0.012 inches.

4. The work tool assembly of claim 1, 2 or 3 wherein said tube is formed of an austenitic stainless steel.

5. The work tool assembly of claim 1, 2 or 3 wherein said tube is formed of an austenitic stainless steel and said tool is formed of a martensitic stainless steel.

6. The work tool assembly of claim 5 wherein the austenitic stainless is type 302, 303, 304 or 316 and the martensitic stainless steel is type 416 or 440C.

7. The work tool assembly of claim 1, 2 or 3 wherein the inner surface finish of said tube is smoother than about 25 micro-inches.

8. The work tool assembly of claim 7 wherein said tube is formed on an austenitic stainless steel.

9. The work tool assembly of claim 7 wherein said tube is formed of an austenitic stainless steel and said tool is formed of a martensitic stainless steel.

10. The work tool assembly of claim 9 wherein the austenitic stainless steel is type 302, 303, 304 or 316 and the martensitic stainless steel is type 416 or 440C.

11. The work tool assembly of claim 1, 2 or 3 wherein said groove is V-shaped.

12. The work tool assembly of claim 11 wherein said tube is formed of an austenitic stainless steel.

13. The work tool assembly of claim 11 wherein said tube is formed of an austenitic stainless steel and said tool is formed of a martensitic stainless steel.

14. The work tool assembly of claim 13 wherein the austenitic stainless steel is type 302, 303, 304 or 316 and the martensitic stainless steel is type 416 or 440C.

15. A dental scaler comprising:
   elongated casing means having a proximal end and a distal end;
   resilient support means within said casing means;
   a substantially rigid hollow shaft supported within said elongated casing means by said resilient support means;
   work tool assembly means detachably connected to the distal end of said hollow shaft, said work tool assembly means comprising a hollow body having a first end and a second end, said first end being adapted for detachable connection with said hollow shaft and having a first orifice therein, said second end of said body having a second orifice therein, a tube having a first end and a second end, said tube extending continuously from said first end of said body to said second end of said body, said second end of said tube terminating substantially adjacent to the second end of said body, said first end of said tube being located within said first orifice and terminating flush with said first end of said body, and a work tool having a first end and a second end, said first end being adapted for insertion into said second end of said body within said second orifice, said second end of said tool being adapted for performing an operative function on a tooth surface, said tool having a groove on the outer surface thereof extending from said second end of said tool to a position intermediate said first and second ends of said tool and outwardly of said second end of said body, a portion of said tube lying within said groove between said tool and said body;

means for imparting vibration to said resiliently supported hollow shaft when said dental scaler is energized to provide vibratory movement to said work tool;

water transport means comprising a water transport tube disposed substantially coaxially within said hollow shaft, said water transport tube having a proximal end and a distal end; and a water seal assembly for supporting the distal end of said water transport tube within said hollow shaft, said water transport means delivering water from the proximal end of said casing to the first end of said body, and said tube in said work tube assembly delivering water to the outer surface of said work tool, whereby water is transferred along the outer surface of said work tool to said second end of said work tool.

16. The dental scaler of claim 15 wherein said tube in said work tool assembly has an internal diameter of between about 0.010 and 0.018 inches.

17. The dental scaler of claim 16 wherein said tube in said work tool assembly has an internal diameter of about 0.012 inches.

18. The dental scaler of claim 17 wherein the inner surface finish of said tube in said work tool assembly is smoother than about 25 micro-inches.

19. The dental scaler of claim 18 wherein said groove is V-shaped.

20. The dental scaler of claim 19 wherein said tube in said work tool assembly is formed of an austenitic stainless steel.

21. The dental scaler of claim 19 wherein said tube in said work tool assembly is formed of an austenitic stainless steel and said tool is formed of a martensitic steel steel.

22. The dental scaler of claim 21 wherein the austenitic stainless steel is type 302, 303, 304 or 316 and the martensitic stainless steel is type 416 or 440C.

* * * * *